US006624114B1

(12) United States Patent
Eberle et al.

(10) Patent No.: US 6,624,114 B1
(45) Date of Patent: Sep. 23, 2003

(54) SUPPORTED CATALYSTS AND THEIR USE IN THE GAS-PHASE OXIDATION OF HYDROCARBONS

(75) Inventors: Hans-Jürgen Eberle, München (DE); Dirk Groke, Taufkirchen (DE); Christoph Rüdinger, Starnberg (DE); Ulrich Wecker, Eurasburg (DE)

(73) Assignee: Consortium fur Elektrochemische Industrie GmbH, Munich (DE)

( * ) Notice: Subject to any disclaimer, the term of this patent is extended or adjusted under 35 U.S.C. 154(b) by 90 days.

(21) Appl. No.: 09/709,832

(22) Filed: Nov. 10, 2000

(30) Foreign Application Priority Data

Dec. 9, 1999 (DE) .......................... 199 59 413

(51) Int. Cl.⁷ ............................... B01J 32/00
(52) U.S. Cl. .................... 502/439; 502/527.24; 261/94; 261/DIG. 72; 422/312
(58) Field of Search ...................... 261/94–98, DIG. 72; 502/309, 312, 321, 350, 353, 439, 527.24; 562/607; 422/312

(56) References Cited

U.S. PATENT DOCUMENTS

| 2,408,164 A | | 9/1946 | Foster |
| 3,284,762 A | * | 11/1966 | Kompanek et al. ........... 340/11 |
| 3,966,644 A | | 6/1976 | Gustafson |
| 4,328,130 A | | 5/1982 | Kyan |
| 4,370,261 A | | 1/1983 | Wunder et al. |
| 4,370,492 A | | 1/1983 | Wunder et al. |
| 4,402,870 A | * | 9/1983 | Schurmans .................. 428/156 |
| 4,645,754 A | | 2/1987 | Tamura et al. |
| 4,656,157 A | | 4/1987 | Hofmann et al. |
| 5,677,261 A | | 10/1997 | Tenten et al. |
| 6,117,812 A | * | 9/2000 | Gao et al. .................... 502/155 |

FOREIGN PATENT DOCUMENTS

| DE | 3445289 | 6/1986 |
| DE | 69101032 | 1/1994 |
| DE | 69/11612 | 7/1995 |
| DE | 197 21 368 | 11/1998 |
| EP | 0004079 | 9/1979 |
| EP | 0220933 | 5/1987 |
| EP | 0464633 | 1/1994 |
| EP | 0552287 | 7/1995 |
| EP | 0714700 | 8/1998 |
| GB | 1 373 351 | 11/1974 |
| GB | 2193907 | 2/1988 |
| GB | 2 197 597 | 5/1988 |
| WO | 98/52688 | 11/1998 |

OTHER PUBLICATIONS

European Search Report.

* cited by examiner

Primary Examiner—Steven Bos
Assistant Examiner—Anthony Kuhar
(74) Attorney, Agent, or Firm—Brooks & Kushman P.C.

(57) ABSTRACT

The invention relates to supported catalysts consisting of an active material on an inert support in the shape of rings, wherein the rings have one or more notches in the upper and/or lower flat side of the ring.

14 Claims, 2 Drawing Sheets

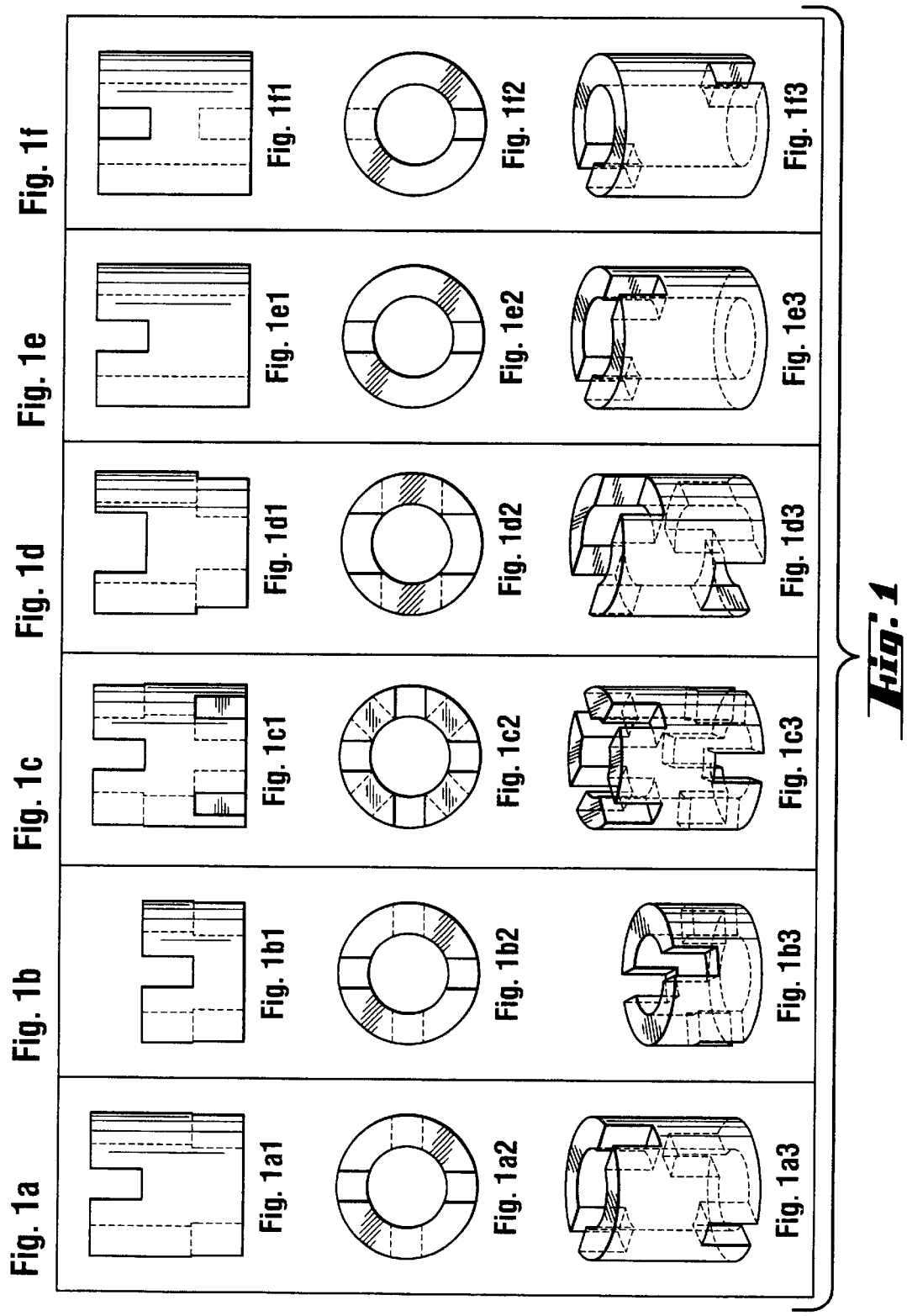

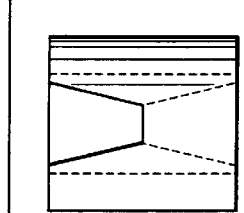
Fig. 2a1
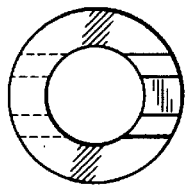
Fig. 2a2
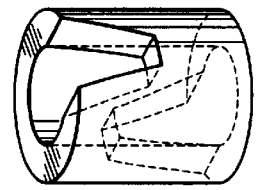
Fig. 2a3
Fig. 2a
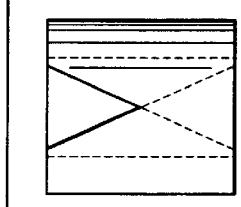
Fig. 2b1
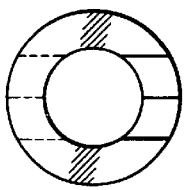
Fig. 2b2
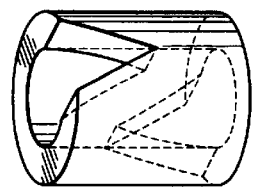
Fig. 2b3
Fig. 2b
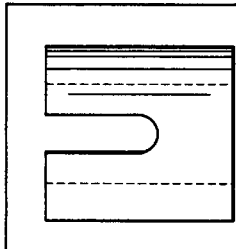
Fig. 2c1
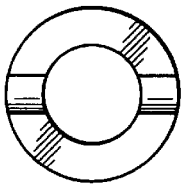
Fig. 2c2
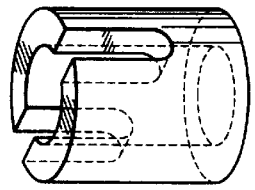
Fig. 2c3
Fig. 2c
Fig. 2

SUPPORTED CATALYSTS AND THEIR USE IN THE GAS-PHASE OXIDATION OF HYDROCARBONS

BACKGROUND OF THE INVENTION

1) Field of the Invention The invention relates to supported catalysts and their use in the gas-phase oxidation of hydrocarbons.

2) Background Art

Supported catalysts for the gas-phase oxidation of hydrocarbons to the corresponding oxidation products, such as, for example, carboxylic acids, carboxylic anhydrides or aldehydes, have long been known. A typical example of use of such catalysts is the preparation of phthalic anhydride from o-xylene or naphthalene, maleic anhydride from benzene or butane, formaldehyde from methanol, or acrylic acid or acrolein from propene. Recently, the preparation of acetic acid by the oxidation of ethane or butane or butene and butane/butene mixtures using supported catalysts has also been described. Common to all these preparation processes is the fact that the reactions are highly exothermic. For this reason, virtually all such processes are carried out in so-called tubular reactors. Here, the tubes are filled with a catalyst and removal of the resulting heat of reaction (cooling) is usually effected by means of a salt melt with which the reaction tubes inside the reactor are surrounded. Depending on the temperature range, the cooling can alternatively also be effected by means of steam, superheated water or other heat-transfer liquids.

The catalysts used are predominantly supported catalysts which, as a rule, consist of an inert support, for example of annular or spherical shape, on which the actual catalytically active material is applied. In the case of the phthalic anhydride and acetic acid catalysts, such catalytically active materials predominantly consist of, for example, $TiO_2$ in the anatase form and $V_2O_5$. For improving the control of the activity and improving the selectivity, additionally activating or damping additives, for example oxides of elements of the subgroups of the Periodic Table, alkali metal compounds and/or, in small amounts, promoters are frequently mixed as dopants with the catalytically active material. In the case of catalysts for the preparation of maleic anhydride, the catalytically active material consists of, for example, vanadyl pyrophosphate.

In the preparation of the supported catalysts, in general, suspensions of catalyst powder and liquids (water, organic solvents) or solutions or suspensions of the individual catalyst components, if required with the addition of binder for improving the adhesion of the active components on the support, are sprayed onto the supports.

Furthermore, EP-B 714700 (U.S. Pat. No. 5,677,261) discloses the application of dry powder to moistened supports.

The supports usually used are regularly shaped, mechanically stable bodies, such as spheres, rings, half-rings or saddles. The size of the supports is determined predominantly by the reactor dimensions, especially by the internal diameter of the individual reaction tubes. Support materials used are, for example, steatite, duranite, earthenware, silica, silicon carbide, aluminates, metals and metal alloys.

In choosing the shape of the support and its dimensions, in particular, the associated pressure drop plays an important role. A small pressure drop across the catalyst bed can mean a considerable energy saving, for example in the case of the fan energy.

A further criterion is that the support materials can be produced as economically as possible. Rings and spheres have become established in industry, annular supports being increasingly used owing to the smaller pressure drop present in the case of the rings.

In the past, there has been no lack of attempts, by varying the ring shape, to find support materials which have an optimum pressure drop (i.e., as low a pressure drop as possible) and carry as much active material as possible, but without adversely affecting the other performance data such as selectivity, stability, productivity, etc.

DE-A 344 5289 (U.S. Pat. No. 4,656,157) describes, for example, an annular support which differs from "normal rings" in that its end faces are rounded. This annular support is said to permit more uniform filling of the reaction tubes and hence a more uniform course of the reaction. Nothing is stated with regard to the pressure build-up.

EP-B 552287 discloses an unsupported catalyst for the preparation of maleic anhydride, which catalyst consists of a solid geometric shape in which at least one cavity is arranged in its outer surface. The examples describe exclusively shapes in which the cavities are arranged in the outer surfaces and not in the end faces. The aim of these shapes is to obtain as large a surface area of the unsupported catalysts as possible. The shapes shown can be realized technically only with great effort and at high costs.

EP-A 220933 discloses an unsupported catalyst for use in catalytic processes, which catalyst has a "four-winged" shape. This shape is obtained by extruding the catalyst material. Owing to its specific shape, the catalyst has better physical properties with respect to breaking strength and pressure build-up.

GB-A 2193907 describes a catalyst of cylindrical shape whose outer surface is provided, in the longitudinal direction, with ribs which are dimensioned and arranged in such a way that the individual catalyst body cannot interlock.

U.S. Pat. No. 4,328,130 likewise describes a catalyst shape in which a plurality of channels and ribs run along the longitudinal direction of a cylinder, the recesses being narrower than the ribs in order to avoid interlocking.

EP-A 004079 (U.S. Pat. No. 4,370,492 and U.S. Pat. No. 4,370,261) discloses catalyst shapes which are extruded sections having a star-shaped cross-section or are ribbed extrudates.

U.S. Pat. No. 3,966,644 describes catalyst shapes comprising extrudates in the form of a plurality of cylinders joined parallel to one another.

Those forms for catalyst supports which are described in the prior art and permit reduced pressure build-up all have very complicated shapes. The preparation generally entails high costs and is therefore uneconomical on an industrial scale.

Many of these complicated shapes, which are obtainable in particular by extrusion, are unsuitable for coating by means of active catalyst material owing to their surface and therefore can be used only as unsupported catalyst.

The object was therefore to provide catalyst supports which, on the one hand, have a smaller pressure build-up than conventional rings or spheres in the reactor but, on the other hand, have a highly geometric and hence coatable surface which however is as simple as possible. In addition, these support shapes should be simple and economical to prepare and should differ geometrically from the industrially used supports only to an insignificant extent, in order to be able to use them without problems in existing oxidation plants and processes. Furthermore, the supported catalysts to be developed should have just as good a stability as those known from the prior art, should be capable of being introduced into the reaction tubes by means of the known filling machines and should permit a uniform coat thickness when coated with the active material.

SUMMARY OF THE INVENTION

The invention relates to supported catalysts consisting of an active material on an inert support in the shape of rings, wherein the rings have one or more notches in the upper and/or lower flat side of the ring.

BRIEF DESCRIPTION OF THE DRAWINGS

FIG. 1 illustrates six embodiments (a–f) of the supported catalysts of the subject invention, in side, sectional, and isometric views;

FIG. 2 illustrates three additional embodiments (a–c) in side, sectional, and isometric views.

DETAILED DESCRIPTION OF THE PREFERRED EMBODIMENTS

The number of notches on the flat sides of the catalyst according to the invention depends on the requirements of the corresponding reaction and on the dimensions of the annular supports. At least one flat side of the ring is provided with at least one notch. Preferred supports are those in which each of the two flat sides of the ring is provided with one or more notches. Catalysts having 2 to 8 notches on each flat side, particularly preferably 2 to 4 notches, are preferred.

The size of the rings used depends primarily on the requirements, i.e., on the size of the reactor. The support diameter should be between ½ and ¹/₁₀ of the internal diameter of the reaction tubes, preferably between ⅓ and ⅕. Suitable materials are, for example, steatite, duranite, silicon carbide, earthenware, porcelain, silica, silicates, alumina, aluminates or mixtures of these substances. These may be dense-sintered or may have a porous structure. Rings of steatite (dense-sintered magnesium silicate) having a height of from 4 to 10 mm, an external diameter of from 6 to 10 mm and a wall thickness of from 1 to 2 mm are preferably used.

The notches according to the invention on the respective sides may be regularly or irregularly distributed. The arrangement of the notches on the flat sides of the rings is preferably chosen so that the notches on the opposite sides are always "in gaps". For example, in a catalyst according to the invention which has in each case two notches on each flat side, the notches are thus arranged offset by 90 degrees on the opposite flat side.

The shape of the notches may be semicircular, rectangular, trapezoidal or V-shaped.

In designing the notches, it is advantageous if the individual notches are slightly smaller or substantially larger than the ring thickness. In this way, it is possible to avoid interlocking, which, inter alia, complicates the coating process. The depth and the width of the notches are determined by the mechanical stability of the support. The dimensions of the notches must be at least sufficiently large so that the notches are not closed by active material during coating. The maximum notch depth and also the width of the notch are limited by the fact that no destruction of the catalyst may occur during the further preparation steps as well as at steps during use (reactor filling).

Notches having a depth of ⅓ to ½ of the height of the annular body are preferred if notches are provided at the top and bottom. If only one side of the catalyst is provided with the notches according to the invention, the depth of the notches may also be greater than half the depth of the annular body. After all, the maximum notch depth is dependent on the remaining stability of the support.

By providing two notches each in the upper and lower end face of the ring, the pressure drops can be reduced by about 30% without thereby resulting in a significant loss of coatable surface.

Thus, the subject invention pertains to a supported catalyst comprising a ring having opposite ends and inner and outer surfaces defining a wall thickness, the ring having at least one notch extending between the inner and outer surfaces, having an open extremity at one of the ends of the ring, and a closed extremity spaced from the other end of the ring. A catalytic material is coated on surfaces of the ring.

Surprisingly, using the gas-phase oxidation of butane, butene and mixtures thereof to acetic acid as an example, it has been possible to show that the catalysts according to the invention additionally resulted in a substantial increase of 4% in the selectivity in the reaction of the starting materials, apart from having the advantage of reduced pressure build-up in the reactor. Furthermore, it was also observed that the formation of hot spots in the main reaction zone was substantially reduced, as shown by the examples of the o-xylene oxidation to phthalic anhydride.

The invention is to be explained in more detail with reference to the following examples.

EXAMPLE 1

(Shape Examples)

FIGS. 1a–f show some shape examples of the catalyst according to the invention, having different numbers and arrangements of the notches. The catalyst body is shown in each case as a side view (1), a plan view (2) and a perspective view (3):

a.) Two notches each in the upper and lower sides, offset 90° relative to one another, notch depth ⅓ of the ring height, notch width smaller than ring thickness.

b.) Two notches each in the upper and lower sides, offset 90° relative to one another, notch depth ½ of the ring height, notch width smaller than ring thickness.

c.) Four notches each in the upper and lower sides, offset 45° relative to one another, notch depth ⅓ of the ring height, notch width smaller than ring thickness.

d.) Two notches each in the upper and lower sides, offset 90° relative to one another, notch depth ⅓ of the ring height, notch width greater than ring thickness.

e.) Two notches on one side, notch depth ⅓ of the ring height, notch width smaller than ring thickness.

f.) One notch each in the upper and lower sides, offset 180° relative to one another, notch depth ⅓ of the ring height, notch width smaller than ring thickness.

FIGS. 2a–c show some examples of the catalyst according to the invention, having different geometric shapes of the notches. The catalyst body is shown in each case as a side view (1), a plan view (2) and a perspective view (3):

a.) U-shaped notch
b.) V-shaped notch
c.) Trapezoidal notch

EXAMPLE 2

(Pressure Drop Measurements)

A measuring apparatus having a tube length of 348 cm, an internal diameter of 25 mm, a pressure controller (0–7.5 bar), a rotameter (0–5 m³ (S.T.P.)/h), a precompression chamber and a dynamic pressure manometer was filled with catalyst rings. The fill height was 280 cm for the rings A, B, C and D, and 72 cm for the rings E and F.

For the dynamic pressure measurement, the network air pressure (6 bar) was reduced to 2.5 bar by means of a pressure controller. The required air flow rates (3 and 4 m³ (S.T.P.)/h) with an admission pressure of 1.5 bar were set at the rotameter. The pressures could then be read on the dynamic pressure manometer. The measurement was carried out at room temperature.

The measurement was carried out using coated (C, D) and uncoated (A, B) catalyst rings. The coated rings were coated in each case with 8% by weight of catalytic material, consisting of $V_2O_5/TiO_2$. Notched rings having in each case two notches in the upper side and two notches in the lower side were used (A, C). The notches were offset by 90 degrees relative to one another. The ring had dimensions of 7×7×4 mm (external diameter×height×internal diameter), the notch width was 1.4 mm and the notch depth was 2 mm. For comparison, rings which had dimensions of 7×7×4 mm and were not provided with notches were measured.

In addition, smaller rings having dimensions of 7×4×4 mm were measured (E). These rings were provided with two rectangular notches on each side. The notches were offset by 90 degrees relative to one another and had in each case a depth of 2 mm and a width of 1.4 mm. For comparison with these, rings which had the same dimensions but no notches were measured (F).

The results of these measurements are shown in Table 1 and Table 2.

TABLE (1)

| | | Pressure (bar) at 3 m³ (S.T.P.)/h | Pressure (bar) at 4 m³ (S.T.P.)/h |
|---|---|---|---|
| A | Notched rings Uncoated 7 × 7 × 4 mm | 0.069 | 0.106 |
| B | Rings without notches Uncoated 7 × 7 × 4 mm | 0.082 | 0.128 |
| C | Notched rings Coated 7 × 7 × 4 mm | 0.064 | 0.099 |
| D | Rings without notches Coated 7 × 7 × 4 mm | 0.079 | 0.120 |
| E | Notched rings Uncoated 7 × 4 × 4 mm | 0.026 | 0.039 |
| F | Rings without notches Uncoated 7 × 4 × 4 mm | 0.038 | 0.059 |

TABLE (2)

| | Δp (bar) at 3 m³ (S.T.P.)/h | Δp (%) at 3 m³ (S.T.P.)/h | Δp (bar) at 4 m³ (S.T.P.)/h | Δp (%) at 4 m³ (S.T.P.)/h |
|---|---|---|---|---|
| p(B-A) | 0.012 | 18.8 | 0.022 | 20.8 |
| p(D-C) | 0.015 | 23.4 | 0.021 | 21.2 |
| p(F-E) | 0.012 | 32 | 0.02 | 34 |

The tabulated evaluation of the test results clearly shows that the catalysts according to the invention result in a smaller pressure build-up than conventional catalysts without notches. Catalysts according to the invention having a size of 7×7×4 mm produce about 20% less pressure build-up; in the case of smaller rings measuring 7×4×4 mm, this effect is even up to 34% greater.

EXAMPLE 3

(Preparation of the Catalyst According to the Invention for the Synthesis of Phthalic Anhydride)

For the preparation of the catalysts, 11.3 g of $V_2O_5$, 70.8 g of $TiO_2$ (BET 8 m²/g), 17.7 g of $TiO_2$ (BET 200 m²/g) and 0.2 g of cesium (as $CsCO_3$) were suspended in 400 ml of demineralized water and stirred for 18 hours to obtain a homogeneous distribution. 1.5 g of organic binder, consisting of a copolymer of vinyl acetate and vinyl laurate in the form of a 50% strength by weight aqueous dispersion, were added to this suspension. The suspension obtained was then sprayed onto 1203 g of steatite rings, having in each case two notches in the upper side and two notches in the lower side, and was dried. The notches were offset by 90 degrees relative to one another. The rings had dimensions of 7×7×4 mm and the notch width was 1.4 mm and the notch depth 2 mm.

COMPARATIVE EXAMPLE 1

(Catalyst From Example 3 on Rings Without Notches)

A catalyst was prepared analogously to Example 3, except that it was applied to steatite rings of a size 7×7×4 mm and without notches.

EXAMPLE 4

(Preparation of a Catalyst According to the Invention for the Synthesis of Acetic Acid)

The preparation of the catalyst was carried out analogously to DE-A-19649426. The active material consisted of oxides of titanium, vanadium, molybdenum and antimony of the empirical formula $Ti_aV_bMo_cSb_dO_e$ (a: 91; b: 7; c: 1; d: 3; e: 207) and was coated in an amount of 14.4% by weight plus 1.6% by weight of graphite, based on the weight of the support. This active material was applied to the notched steatite rings having in each case two notches in the upper side and two notches in the lower side and was dried. The notches were offset by 90 degrees relative to one another. The rings had dimensions of 7×7×4 mm, the notch width was 1.4 mm and the notch depth 2 mm.

COMPARATIVE EXAMPLE 2

(Catalysts From Example 4 on Rings Without Notches)

The preparation of the catalyst was carried out analogously to Example 4, except that the active material was applied to rings without notches and having dimensions of 7×7×4 mm (external diameter×internal diameter×height).

EXAMPLE 5

(Testing of the Catalysts From Example 3 and Comparative Example 1 Using the O-xylene Oxidation as an Example)

The test was carried out in a tubular reactor having a length of 330 cm and an internal tube diameter of 25 mm. The tube was thermostated by a circulated salt bath (eutectic melt comprising potassium nitrate and sodium nitrite). The reactor was filled with the catalyst according to the invention, from Example 3, or with the catalyst from Comparative Example 1. The height of fill of the catalyst was 280 cm in both experiments. The salt bath temperature was 365° C. After the filling, 4 m³ (S.T.P.) of an air/o-xylene mixture were passed through this reactor, the o-xylene concentration being 60 g/m³ (S.T.P.) of air and the air/o-xylene mixture being preheated to 180° C. before entering the reactor. A thermocouple which permitted measurement of the temperature variation in the tube was installed centrally in the reactor.

The reaction gas leaving the reactor was passed through a desublimator in order to separate off the reaction products, such as phthalic anhydride.

The results of the experiments are shown in Table 3 below.

TABLE (3)

Results of the o-xylene oxidation experiments

| | Pressure drop at 4 m³ (S.T.P.)/h | Yield of phthalic anhydride in % by weight | Maximum temperature in the catalyst bed in °C. (= hot spot) |
|---|---|---|---|
| Catalyst according to the invention | 0.33 bar | ~113 | 434 |
| Comparative catalyst | 0.40 bar | ~111 | 449 |

The results in Table (3) show that the notched catalyst according to the invention has a substantially smaller pressure drop. The product yield is also better in the case of the catalyst according to the invention. On the basis of the comparison of the maximum temperatures (hot spot) in the reaction tube, it can be seen that the catalyst according to the invention surprisingly additionally has a lower hot-spot temperature.

EXAMPLE 6

(Testing the Catalyst From Example 4 and Comparative Example 2 Using the Oxidation of Butane/Butene Mixtures to Give Acetic Acid as an Example)

The catalyst according to the invention, from Example 4, was introduced into a circulation gas reactor having an internal reaction tube diameter of 25 mm, with a height of fill of 6000 mm, and was tested according to DE-A 19910866, using an oxidation of a butene/butane mixture as an example. 320 g/h of oxygen, 130 g/h of 1-butene and 56 g/h of n-butane were fed in as reaction gas. The circulation gas flow was adjusted so that the reactor reached a circulation gas flow of 12,780 g/h in the stable state. The reactor was operated at a pressure of $11 \times 10^5$ Pa and a coolant temperature of 187° C.

The separation of the acid from the reaction gas was effected by absorption with 1000 g/h of water (added at the top) in an absorber having a structured packing, an internal diameter of 43 mm and a packing height of 3240 mm at an absorber top temperature of 130° C. Under these conditions, a butene conversion of 99.8% and a butane conversion of 83.1% were achieved.

The acetic acid selectivity relative to the total $C_4$ conversion was 73 mol % and the formic acid selectivity relative to the total $C_4$ conversion was 9 mol %. The crude acid concentration was 24% by weight.

In a further experiment, the procedure was analogous to the above method using the comparative catalyst from Comparative Example 2 (333 g/h of oxygen, 130 g/h of 1-butene and 60 g/h of n-butane). The circulated gas flow was adjusted so that the reactor reached a circulation gas flow of 12,520 g/h in the stable state. The reactor was operated at a pressure of $11 \times 10^5$ Pa and a coolant temperature of 191° C.

The separation of the acid from the reaction gas was effected by absorption with 1000 g/h of water (added at the top) in an absorber having a structured packing, an internal diameter of 43 mm and a packing height of 3240 mm at an absorber top temperature of 130° C.

Under these conditions, a butene conversion of 99.8% and a butane conversion of 83.8% were achieved. The acetic acid selectivity relative to the total $C_4$ conversion was 70 mol % and the formic acid selectivity relative to the total $C_4$ conversion was 8 mol %. The crude acid concentration was 23% by weight.

These results show that the notched catalyst according to the invention surprisingly gave an acetic acid selectivity 3 mol % higher and a formic acid selectivity 1% higher under virtually identical experimental conditions. This gives 4% higher total acid selectivity of this reaction. At the same time, the pressure drop of the catalyst packing was about 20% less than that of the comparative catalyst. This fact indicates an enormous energy saving in such reactions.

What is claimed is:

1. A supported catalyst, comprising:
   a) a ring having opposite ends and inner and outer surfaces extending between the outer ends, the inner and outer surfaces defining a wall thickness, said ring having at least one notch extending between the inner and outer surfaces, said notch having an open extremity at one of the ends of the ring and having a closed extremity spaced from the other end of the ring; and
   b) a catalytic material coated on surfaces of said ring.

2. The supported catalyst of claim 1, wherein the ring has from 2 to 8 notches.

3. The supported catalyst of claim 1, wherein the catalytic material comprises a catalyst suitable for the gas phase oxidation of hydrocarbons.

4. The supported catalyst of claim 1 having at least one notch on each end of the ring, notches on one end of the ring offset radially from notches on the other end of the ring.

5. The supported catalyst of claim 1 having a plurality of notches, said notches being disposed radially in a regular geometric pattern.

6. The supported catalyst of claim 1, wherein said notch extends from ⅓ to ½ the length of said ring.

7. The supported catalyst of claim 1, wherein said notch has a shape which is semicircular, rectangular, trapezoidal, or V-shaped.

8. The supported catalyst of claim 1, wherein the smallest dimension of the notch width at the end of the ring is greater than the wall thickness of the ring.

9. The supported catalyst of claim 1, wherein the smallest dimension of the notch width at the end of the ring is smaller than the wall thickness of the ring.

10. The supported catalyst of claim 1, wherein the width of the notch at the end of the ring is selected such that interlocking of a ring wall with a notch of another ring is prevented.

11. The supported catalyst of claim 1, wherein the ring is comprised of a ceramic substance selected from the group consisting of steatite, silicon carbide, earthenware, porcelain, silica, silicates, alumina, aluminates, and mixtures thereof.

12. The supported catalyst of claim 1, wherein the ring has a circular cross-section, a length between ends thereof of from 4 to 10 mm, an external diameter of from 6 to 10 mm, and a wall thickness of 1 to 2 mm.

13. The supported catalyst of claim 1, wherein said catalytic material comprises a catalyst for the gas-phase oxidation of o-xylene, naphthalene, or mixtures thereof, to phthalic anhydride.

14. The supported catalyst of claim 1, wherein said catalytic material comprises a catalyst for the gas-phase oxidation of hydrocarbons.

* * * * *